Figure 1:
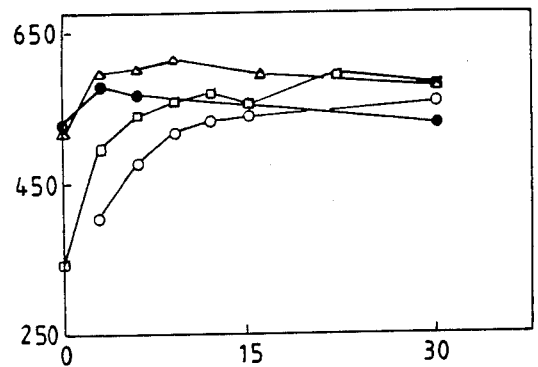
Figure 1:
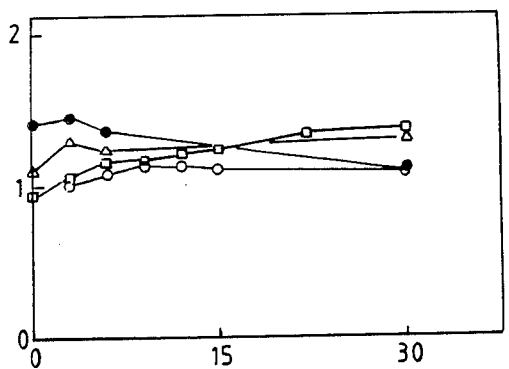

United States Patent [19]

Armstrong et al.

[11] Patent Number: 4,857,152

[45] Date of Patent: Aug. 15, 1989

[54] PEROXIDE ELECTRODES

[75] Inventors: Fraser A. Armstrong, Ramsden; Anthony M. Lannon, Manchester, both of Great Britain

[73] Assignee: Medisense, Inc., Cambridge, Mass.

[21] Appl. No.: 196,039

[22] Filed: May 19, 1988

[30] Foreign Application Priority Data

May 19, 1987 [GB] United Kingdom ............. 8711736

[51] Int. Cl.$^4$ ................................................ C12Q 1/28
[52] U.S. Cl. ................................. 204/1 T; 204/403; 435/28; 435/817
[58] Field of Search ............... 435/28, 817; 204/1 E, 204/403

[56] References Cited

FOREIGN PATENT DOCUMENTS 3342977 6/1985 Fed. Rep. of Germany .

Primary Examiner—G. L. Kaplan

[57] ABSTRACT

Hydrogen peroxide can be detected using a pyrolytic graphite edge electrode when cytochrome c peroxidase and an aminoglycoside are both present in the system.

12 Claims, 1 Drawing Sheet

PEROXIDE ELECTRODES

The present invention relates to graphite electrodes coated to facilitate detection of a substrate in solution, to kits for making such electrodes, and to methods of assay using the electrodes.

Detection of hydrogen peroxide ($H_2O_2$) is, in theory, possible at an electrode by measurement of the current required for its reduction. Specific detection is possible only when an $H_2O_2$-specific catalyst is used. Such a specific catalyst occurs naturally, in the form of cytochrome c peroxidase (CCP). However, macromolecules, such as CCP, are unable to interact with known electrode surfaces and, so, are unavailable for use in $H_2O_2$-sensitive electrodes.

We have now discovered that fast interfacial electron transfer between cytochrome c peroxidase and a pyrolytic graphite edge (PGE) electrode can be achieved by addition of aminoglycosides to the system.

Thus, according to a first aspect of the present invention, there is provided a hydrogen peroxide-sensitive electrode comprising a pyrolytic graphite edge (PGE) electrode at least partially coated with a mixture of an aminoglycoside and CCP.

The CCP used in accordance with the invention is preferably obtained from cultures of microorganisms, such as baker's yeast, but any means is acceptable.

Suitable aminoglycosides for use in accordance with the invention are gentamycin and neomycin, especially gentamycin $C_{1a}$ and neomycin B. However, other suitable aminoglycosides, apparent to those skilled in the art, may be used.

The aminoglycoside provides the necessary link between CCP and the PGE electrode surface. Thus, in preparation, it is preferred that the PGE electrode be treated with aminoglycoside first, although addition with, or even after, addition of CCP still yields acceptable results.

The PGE electrode may be coated with aminoglycoside and CCP as desired. In a preferred embodiment, the two components are added sequentially, or together in solution, and freeze-dried. In an alternative embodiment, the aminoglycoside may be used to provide coated PGE electrodes, with CCP only being introduced at a later stage, for example, in a test solution.

Preparation of a PGE electrode with a primary layer of aminoglycoside is particularly useful, as aminoglycosides are adsorbed onto PGE's, forming stable structures.

In fact, even the aminoglycoside need not be provided until use. Thus, in an alternative aspect of the present invention, there is provided a kit comprising a pyrolytic graphite edge electrode, CCP and an aminoglycoside for use in assaying hydrogen peroxide.

It will be appreciated that the electrodes according to the invention may be incorporated into suitable assay apparatus known in the art, or may incorporate known components to enhance function, such as preservatives for CCP etc.

Furthermore, the present invention provides a method for the detection of hydrogen peroxide, comprising the use of a pyrolytic graphite edge electrode in association with an aminoglycoside and cytochrome c peroxidase.

A typical method for the electrolytic detection of hydrogen peroxide comprises the steps of:

(a) bringing a pyrolytic graphite edge electrode, together with an aminoglycoside and cytochrome c peroxidase, into association with a sample suspected of containing hydrogen peroxide; and (b) detecting the current generated.

It is unlikely that the spatial arrangements of $-NH_3^+$ groups on the aminoglycosides of the present invention, providing a quasi-rigid framework, act to promote the docking of CCP at the PGE surface.

Aminoglycosides, used in accordance with the present invention, induce a stable enzyme-electrode interaction, allowing facile electron transfer to the CCP active site without restricting access to $H_2O_2$. Such features are embodied within the hypothetical model for the CCP-cytochrome c complex (Poulos, T. L., et al., J. Biol. Chem. (1980), 255, 10322–10330.) in which the channel from the molecular surface to the haem crevice is unobscured by cytochrome c bound at a ring of acidic residues (the interaction domain) that surrounds the partly exposed haem edge. It is likely that the electrochemical activity of CCP arises via an analogous configuration assembled at the electrode interface.

The interaction with the electrode is long-lived and produces a saturation coverage of oriented enzyme molecules. Gentamycin and neomycin have charges of $>+3.5$ and $>+4$ respectively at pH 7.4, distributed among discrete $-NH_3^+$ groups, separated by up to 14 Å and 17 Å, which provide a generally flattened area of charge that is broadly complementary to the enzyme interaction domain.

It will be appreciated that the present system demonstrates macromolecular recognition at an electrode interface. Further refinement through variation of glycoside structure is readily available to one skilled in the art, and forms a part of the present invention.

The $H_2O_2$-sensitive electrode of the invention operates efficiently at a significantly small overpotential, and may be used in systems involving the inclusion of interfacial incorporation of other enzymes and biosystems that generate $H_2O_2$.

In general, it will be appreciated that the electrodes of the present invention may be used to detect hydrogen peroxide in both passive and active systems, and may be used to monitor, for example, the activity of oxidoreductases, such as cholesterol, glucose, oxalate and galactose oxidases.

An electrode constructed from aminoglycoside/CCP can be placed in an electrochemical cell containing peroxide alone and 'regular' electroenzymic activity is observed.

Electrodes according to the present invention may be constructed in any manner suitable therefor, such construction, in itself, not forming an essential feature of the invention. Such electrodes may be of any form suitable for use in detection apparatus, or may be formed integrally with such apparatus. In a particularly preferred form, they are embodied in disposable strip form, for one-off analysis of bodily fluids, for example.

Further, such electrodes may be stored in any suitable manner, such as in a dry atmosphere, or away from the atmosphere, or under a gel layer. Such layer may be used to maintain a desirable moisture level, or may contain, for example, aminoglycoside and/or CCP, or be used merely to preclude air.

The following Examples are for the purpose of illustration only and do not limit the invention in any manner.

EXAMPLE 1

In electrolyte alone (0.1M KCl, 5 mM HEPES, pH 7.0), $H_2O_2$ shows no faradaic activity at a polished PGE electrode within the range +850 to +250 mV vs NHE (Normal Hydrogen Electrode).

The electrochemical cell, instrumentation and preparation of PGE electrodes, with suitable modification, were as described in, for example, Armstrong, F. A., et al., J. Amer. Chem. Soc. (1985), 107, 1473–1476. All potentials were converted from SCE (Saturated Calomel Electrode) to NHE using the formula $E_{NHE}$= SCE+250 mV, at 15° C. (at which temperature the reference was maintained). CCP (EC 1:11.1.5) was isolated from baker's yeast according to literature procedures (for example, English, A. M., et al., Inorg. Chim, Acta (1986), 123, 113–116).

Upon addition of CCP (0.2 μM) and gentamycin (5 mM) to the solution at 0° C., a sharp cathodic wave developed with time (between sweeps the diffusion layer was replenished by brief stirring with a microflea at open-circuit potential). The mature wave peaked sharply at +575 mV.

The electrochemistry of the system was stable for at least 1 hour at 0° C. but some instability was observed at 25° C. This may have been due to thermal denaturation at the electrode surface or possibly formation of excessive enzyme coverage, restricting efficient movement of electrons and substrate.

Times required to achieve optimal peak potential varied with [CCP]. Typical results spanned >15 min (0.1 μM) to <3 min (1.0 μM). Corresponding peak currents, corrected for background, were substantially invariant.

No response was observed in the absence of gentamycin, and 1 mM or 5 mM levels yielded the same result, indicative of saturation conditions. Limited studies with neomycin showed a similar response, but $Cr(NH_3)_6^{3+}$, a potent promoter of the electrochemistry of small electron-transfer proteins (EP-A-86302396.6) was much less effective (a broad ill-defined response developed over 15–60 min. incubation times using $Cr(NH_3)_6^{3+}$ in a concentration range of 1–15 mM). Neither gentamycin nor neomycin showed any electrochemical activity alone or with $H_2O_2$ between −800 and +950 mV.

FIG. 1 shows the variation of peak potential (FIG. 1A) and peak current (FIG. 1B) with concentration of CCP; (o) 0.1 μM, (□) 0.2 μM, (Δ) 0.5 82 M, (•) 1.0 μM. Measurements followed addition of CCP (0.2 μM) to a solution of $H_2O_2$ (56 μM) and gentamycin $C_{1a}$ (5 mM) in electrolyte (0.1M KCl, 5 mM HEPES pH 7.0). Sample temperature=0° C., scan rate=10 $mVs^{-1}$. Scans were at 3-minute intervals following the "zero-time" scan. Axes show peak potential (mV vs NHE) and current ($I_p$/μA) vs. time (min's), repsectively. Adjoining lines indicate connectivity. Under this set of conditions a broad feature was consistently observed at around +550 mV on the zero time scan. This probably reflected enhanced catalytic activity stemming from CCP molecules which had already undergone specific adsorption.

EXAMPLE 2

Additions of $H_2O_2$ to the CCP/gentamycin system, appropriately incubated without $H_2O_2$, showed peak currents proportional to [$H_2O_2$] up to 70 μM. Peak potentials increased with decreasing [$H_2O_2$], reaching, typically, +750 mV at 11 μM, (scan rate=10 $mVs^{-1}$, [CCP]=0.2 μM).

Figure 2:
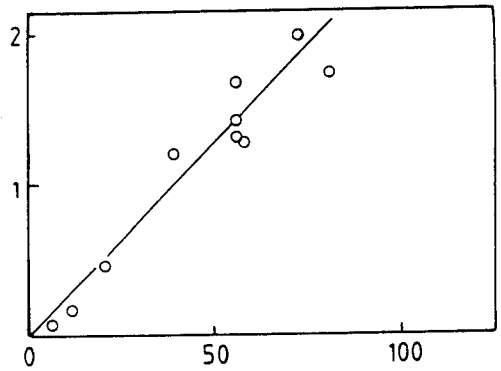

FIG. 2 shows the effect of varying [$H_2O_2$] on the peak current magnitudes. Incubation was with 0.2 μM CCP, and other conditions were as for Example 1. The plot shows current ($I_p$/μA) vs. [$H_2O_2$] (/M×$10^{-6}$).

EXAMPLE 3

Peak current density varied with (scan rate)$^{\frac{1}{2}}$ up to 10 $mVs^{-1}$ and exceeded greatly that appropriate to diffusion of CCP (MW 34000). No catalytic activity appeared with free protoporphyrin IX or metmyoglobin in place of CCP. Thus, the observed results could not be attributed to adsorption of displaced haem (Shigehara, K., et al., J. Phys. Chem. (1982), 86, 2776–2783). Furthermore, horseradish peroxidase (isozyme C), gave only a weak and rather broad response.

Figure 3:
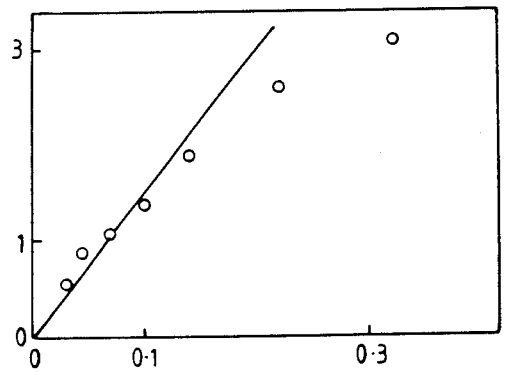

FIG. 3 shows variation of peak current with increasing scan rate (peak current ($I_p$/μA) vs. (scan rate)$^{\frac{1}{2}}$/($Vs^{-1}$)$^{\frac{1}{2}}$). The system was incubated with 0.2 μM CCP, and other conditions were as for Example 1.

The above results show that the reaction continues at the PGE surface until limited by depletion of $H_2O_2$. Under biological conditions the reduction potential for Compound II/Fe(III), estimated using Marcus theory, is 1.09 V and a similar or higher value is likely for Compound I/II. The physiological reaction with cytochrome c (+0.26 V) thus occurs with a formidable driving force ($\Delta E$=0.8–0.9 V). The electrodes of the invention compare very favourably; depletion of local $H_2O_2$ levels at potentials as high as 0.7 V demonstrates that the reaction is driven comfortably at $\Delta E \sim 0.4$ V.

EXAMPLE 4

A polished pyrolytic graphite edge electrode was dipped for 10 minutes in a solution containing 1 mM neomycin/0.5 μM CCP and then rinsed for a further 5 minutes in cold Hepes/KCl (5 mM/100 mM) buffer, pH 7. When the electrode was placed in 54 μM hydrogen peroxide at 0° C., with a scan rate of 20 $mVs^{-1}$, a peak was observed at ca. 270 mV.

EXAMPLE 5

A polished pyrolytic graphite edge electrode was dipped for approximately 5 minutes, first in a 1 mM neomycin solution and then in a 1 μM solution of CCP (both in Hepes buffer, pH 7). The interface was freeze-dried for 30 minutes and then the electrode was placed in a solution of hydrogen peroxide. A response to hydrogen peroxide was observed over the range studied i.e. 10–100 μM.

A measurement taken in the presence of 76 μM $H_2O_2$ (scan rate 10 $mVs^{-1}$) gave a peak at ca. 357 mV.

Freeze-drying followed by immediate use showed that this dry version could respond to increasing levels of hydrogen peroxide.

Freeze-drying of the interface followed by cold dry storage over an 11 day period showed retention of activity, although some reduction in activity was noted.

What we claim is:

1. A hydrogen peroxide-sensitive electrode comprising a pyrolytic graphite edge electrode at least partially coated with a mixture of an aminoglycoside and cytochrome c peroxidase.

2. The electrode of claim 1 wherein said aminoglycoside is selected from the group consisting of gentamycin and neomycin.

3. The electrode of claim 1 wherein said aminoglycoside is selected from the group consisting of gentamycin $C_{1a}$ and neomycin B.

4. The electrode of claim 1 wherein said mixture is freeze-dried onto said electrode.

5. Hydrogen peroxide detection apparatus comprising the electrode of claim 1.

6. A kit comprising a pyrolytic graphite edge electrode, cytochrome c peroxidase and an aminoglycoside, for use in assaying hydrogen peroxide.

7. The kit of claim 6 wherein said aminoglycoside is pre-coated on said electrode.

8. The kit of claim 6 wherein said aminoglycoside is selected from the group consisting of gentamycin and neomycin.

9. The kit of claim 6 wherein said aminoglycoside is selected from the group consisting of gentamycin $C_{1a}$ and neomycin B.

10. A method for electrolytic detection of hydrogen peroxide comprising the steps of:
    (a) bringing a pyrolytic graphite edge electrode, together with an aminoglycoside and cytochrome c peroxidase, into association with a sample suspected of containing hydrogen peroxide; and
    (b) detecting the current generated.

11. The method of claim 10 wherein said aminoglycoside is selected from the group consisting of gentamycin and neomycin.

12. The method of claim 10 wherein said aminoglycoside is selected from the group consisting of gentamycin $C_{1a}$ and neomycin B.

* * * * *